(12) United States Patent
Karlsson

(10) Patent No.: US 6,777,541 B2
(45) Date of Patent: Aug. 17, 2004

(54) PROTEIN PURIFICATION II

(75) Inventor: Göran Karlsson, Vällingby (SE)

(73) Assignee: Octapharma AG (CH)

( * ) Notice: Subject to any disclaimer, the term of this patent is extended or adjusted under 35 U.S.C. 154(b) by 111 days.

(21) Appl. No.: 09/766,098

(22) Filed: Jan. 19, 2001

(65) Prior Publication Data

US 2001/0021770 A1 Sep. 13, 2001

Related U.S. Application Data

(60) Provisional application No. 60/178,355, filed on Jan. 27, 2000.

(30) Foreign Application Priority Data

Jan. 21, 2000 (SE) .............................................. 0000177

(51) Int. Cl.⁷ ........................... A61K 35/14; C07K 1/00
(52) U.S. Cl. ..................................................... 530/393
(58) Field of Search ................................. 530/393, 412, 530/350, 413; 514/2; 435/214

(56) References Cited

PUBLICATIONS

Peterson CB, Blackburn MN. Isolation and characterization of an antithrombin III variant with reduced carbohydrate content and enhanced heparin binding. J Biol Chem. Jan. 10, 1985;260(1):610–5.*

* cited by examiner

Primary Examiner—Karen Cochrane Carlson
Assistant Examiner—Sheridan Snedden
(74) Attorney, Agent, or Firm—Sterne, Kessler, Goldstein & Fox P.L.L.C.

(57) ABSTRACT

The present invention relates to a process for the preparation of a solution comprising a substantially pure isoform of AT-III, said process comprising separating the isoform AT-IIIα from AT-IIIβ on a calcium hydroxyphosphate-based adsorbent.

11 Claims, 1 Drawing Sheet

PROTEIN PURIFICATION II

TECHNICAL FIELD

This application claims the benefit of Provisional application Ser. No. 60/178,355 Filed Jan. 27, 2000.

The present invention relates to processes for the preparation of a solution comprising a substantially pure isoform of AT-III, said process comprising separating the isoform AT-IIIα from AT-IIIβ on a calcium hydroxyphosphate-based adsorbent.

BACKGROUND ART

Antithrombin III (AT-III) is a plasma glycoprotein that inhibits serine proteases in the coagulation cascade and thus plays a major role in the regulation of blood clotting. Antithrombin III is an inhibitor of Factors IXa, Xa, XI, XIIa, and thrombin. Thus, AT-III regulates clot formation in different stages of the coagulation cascade. A small decrease of the AT-III content in the blood is associated with increased risk of thromboembolism. AT-III concentrates are used in the prophylaxis and treatment of thromboembolic disorders in patients with acquired or hereditary antithrombin deficiency. In addition, it has been reported that AT-III is involved in many other biological responses, for example angiogenesis and inflammatory responses. The function of AT-III in these mechanisms is not yet fully understood.

Purification of AT-III with affinity chromatography, using heparin as the solid phase bound ligand, is known in the art. Miller-Andersson et al. (Thrombosis Research 5, 439–452, 1974) discloses the use of heparin-Sepharose to purify human AT-III. The entire procedure, which included ion exchange and gel filtration chromatography, provided a 34% yield.

In human plasma, antithrombin III exists as at least two molecular entities, which are homologous according to amino acid composition, but differ in carbohydrate content and in their heparin-binding behavior. An antithrombin variant, designated as AT-IIIβ, was isolated from human plasma independently from the predominant antithrombin species (designated as AT-IIIα), by virtue of its tight binding to a heparin-Sepharose matrix at high ionic strengths (Peterson, C. B. & Blackburn, M. N. (1985) J. Biol. Chem. 260, 610–615).

The determined molecular weights were 59,800 and 56,900 for human AT-IIIα and AT-IIIβ, respectively. The difference in molecular weights of the two antithrombins was attributed to a reduction of approximately 25–30% in the sialic acid, neutral sugar, and amino sugar content of AT-IIIβ when compared to the carbohydrate content of the AT-IIIα subspecies (Peterson & Blackburn, supra). It has been shown that AT-IIIβ lacks one of the four oligosaccharide side-chains, namely the side-chain at asparagine 135 (Brennan, S. O. et al. (1987) FEBS Letters 219, 431–436). The AT-IIIα form is more negatively charged than AT-IIIβ; it has been demonstrated that AT-IIIα and AT-IIIβ have pI:s of 4.9 and 5.1, respectively (Frebelius, S. et al. (1996) Arteriosclerosis, Thrombosis, and Vascular Biology 16:1292–1297).

It is desirable to obtain pure AT-IIIβ, as this form has specific effects on the coagulation in the vessel wall. It has been shown that AT-IIIβ can prevent restenosis of the rabbit aorta after balloon injury (Swedenborg (1998) Blood Coagulation and Fibrinolysis 9 (suppl. 3):S7–S10). AT-IIIβ may therefore be considered as a potential drug for humans in prophylaxis of restenosis when performing balloon dilatation of the aorta.

Histidine-rich glycoprotein (HRGP) is a single-chained plasma protein originally isolated in 1972. The exact physiological function of HRGP is still unknown. Due to interaction with heparin, fibrinogen and fibrin, plasminogen and activated platelets, HRGP is considered to be a modulator of coagulation and fibrinolysis (Koide, T. In: Fibrinolysis: Current Prospects. Gaffney, PJ (Ed.), John Libbey & Co., London 1988, p.55–63). The polypeptide chain consists of 507 amino acid residues and contains regions that share homology with other plasma proteins, e.g. antithrombin-III (Koide, T. et al. (1986) Biochemistry 25, 2220–2225).

As indicated above, the complete involvement of the two AT-III isoforms and HRGP in the body is not yet fully understood. Consequently, it is desirable to provide efficient purification methods for producing the proteins in pure form, which will facilitate studies in vivo and in vitro.

The use of hydroxyapatite, by means of displacement chromatography, has been disclosed in the purification of antithrombin-III (Freitag & Breier (1995) J. Chromatography A, 691, 101–112). However, the purification of separate isoforms of AT-III has not previously been achieved by hydroxyapatite chromatography.

Figure 1:
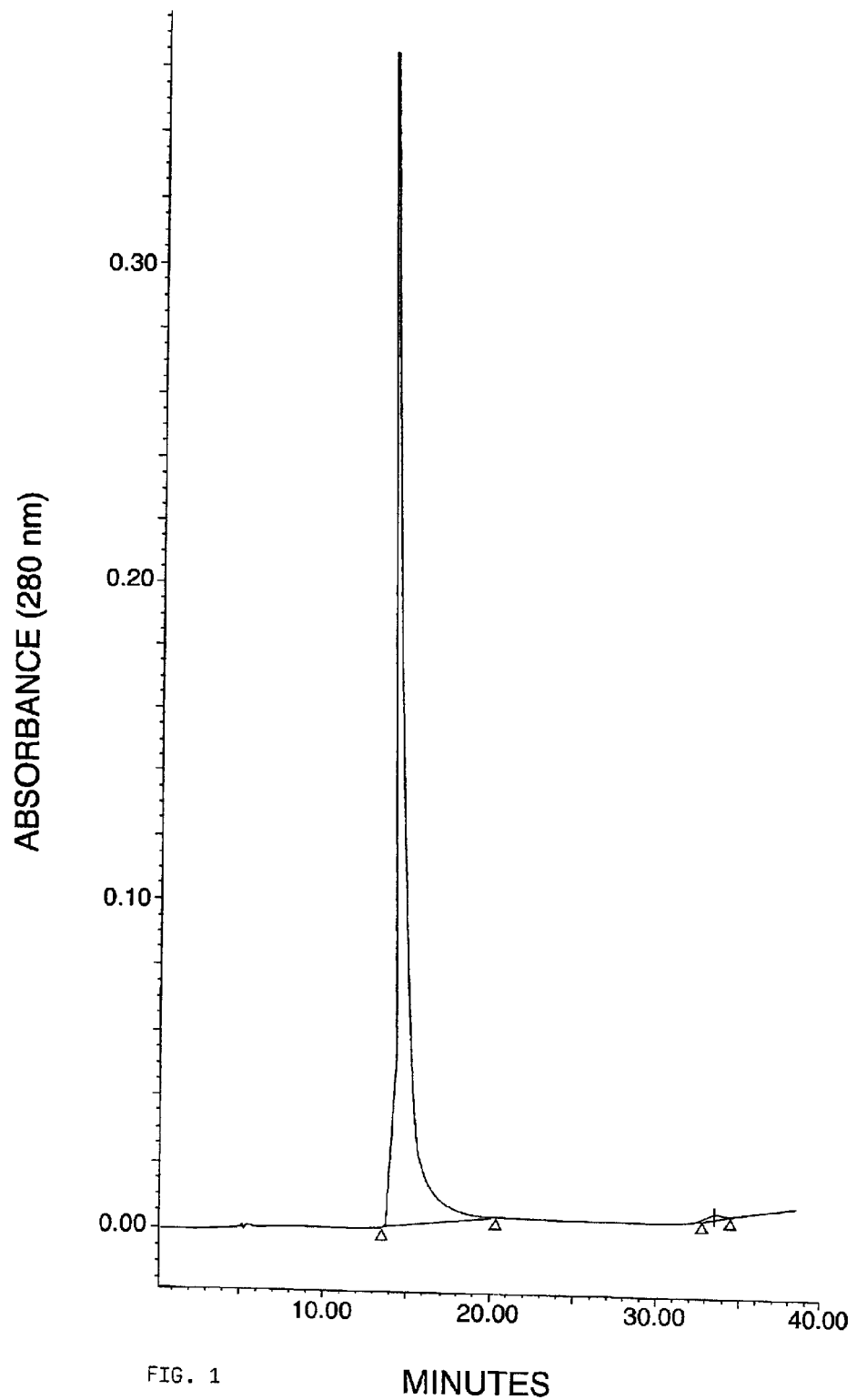
FIG. 1

Separation of AT-IIIα and AT-IIIβ by hydroxyapatite chromatography

DISCLOSURE OF THE INVENTION

It has surprisingly been shown that the antithrombin III isoforms, AT-IIIα and AT-IIIβ, can be conveniently separated and purified using a calcium hydroxyphosphate-based adsorbent.

Consequently, this invention provides in a first aspect a process for the preparation of a solution comprising a substantially pure isoform of AT-III, comprising separating the isoform AT-IIIα from AT-IIIβ on a calcium hydroxyphosphate-based adsorbent. The said process preferably comprising the steps:

(i) preparing a solution mainly comprising AT-III;
(ii) contacting the said solution with the calcium hydroxyphosphate-based adsorbent, preferably hydroxyapatite;
(iii) by adsorption chromatography, preferably column chromatography, eluting and collecting the protein fraction comprising the substantially pure isoform of AT-III.

The said solution mainly comprising AT-III can conveniently be prepared according methods known in the art. A suitable method could e.g. include the steps:

(i) preparing a Cohn Fraction I supernatant from human plasma by known methods (see e.g. Cohn et al. (1946) J. Am. Chem. Soc. 68, 459–475);
(ii) contacting the said Cohn Fraction I supernatant with an affinity gel capable of binding AT-III (see e.g. Koide, T. et al. (1985) J. Biochem. 98, 1191–1200); and
(iii) eluting and collecting the protein fraction binding to the said affinity matrix.

The said affinity gel preferably comprises heparin as the affinity ligand. Suitable affinity gels include heparin-Sepharose® (Amersham Pharmacia); HeparinHyperD (Biosepra), Fractogel TSK AF-Heparin 650 (Merck), Heparin-Agarose (Sigma), TSKgel Heparin (Tosohaas), Heparin-Agarose 6XL (ACL).

As shown in Example 1 below, AT-IIIα is normally eluted from the calcium hydroxyphosphate-based adsorbent with a buffer having a phosphate concentration from about 50 to about 150 mM. AT-IIIβ is normally eluted from the calcium hydroxyphosphate-based adsorbent with a buffer having a phosphate concentration above 150 mM to about 400 mM, preferably from about 200 to about 300 mM. As shown in Example 1 and FIG. 1, AT-IIIα and AT-IIIβ can be collected in fractions eluting from the chromatography column at concentration of about 110 mM and about 250 mM, respectively. The obtained isoform of AT-III is substantially free from histidine-rich glycoprotein (HRGP).

In a further aspect, this invention provides a process for the preparation of a solution comprising a substantially pure histidine-rich glycoprotein (HRGP). This process can be applied when the starting material, in addition to AT-III, also comprises some amount of HRGP, which will normally be the case when the above-described method for preparing AT-III is used (cf. Koide, T. et al. (1985) J. Biochem. 98, 1191–1200). The skilled person will be able to determine the conditions suitable for eluting HRGP from the chromatography column. Under the conditions used in Example 1 below, HRGP will normally be eluted from the column at a phosphate concentration of from about 300 to about 400 mM, such as about 340 mM.

The process according to the invention is normally carried out at a pH from about 6.0 to about 7.5, preferably from about 6.5 to about 7.2, such as about pH 6.8.

The antithrombin preparations produced according to the present invention are suitable as pharmaceutically effective ingredients in pharmaceutical compositions and combinations. The pharmaceutical compositions may optionally comprise additional active ingredients like anti-coagulants such as hirudin or heparin, or thrombolytic agents such as plasminogen activator or hementin. The antithrombin preparations produced according to the invention may form pharmaceutically acceptable salts with any non-toxic, organic or inorganic acid.

The antithrombin preparations produced according to the invention may be administered as unit doses containing conventional non-toxic pharmaceutically acceptable carriers, diluents, adjuvants and vehicles which are typical for parenteral administration. As used herein, the term "pharmaceutically acceptable carrier" means an inert, non toxic solid or liquid filler, diluent or encapsulating material, not reacting adversely with the active compound or with the patient. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

The term "parenteral" includes herein subcutaneous, intra-articular and intratracheal injection and infusion techniques. Also other administrations such as oral administration and topical application are suitable. Parenteral compositions and combinations are most preferably administered intravenously either in a bolus form or as a constant fusion according to known procedures. Tablets and capsules for oral administration contain conventional excipients such as binding agents, fillers, diluents, tableting agents, lubricants, disintegrants, and wetting agents. The tablets may be coated according to methods well known in the art.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives like suspending agents, emulsifying agents, non-aqueous vehicles and preservatives. Topical applications may be in the form of aqueous or oily suspensions, solutions, emulsions, jellies or preferably emulsion ointments.

Unit doses according to the invention may contain daily required amounts of the protein according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance. The object of the treatment, i.e., therapy or prophylaxis and the nature of the thrombotic disease to be treated, antiplatelet or anticoagulant activity.

Experimental Methods

Biological activity (IU/ml) of AT-III was determined as heparin cofactor activity by monitoring the cleavage of the chromogenic substrate H-D-Phe-Pip-Arg-pNA•2 HCl (Chromogenix, Sweden) by thrombin in presence of heparin and AT-III. See Frantzen Handeland et al. (Scand. J. Haematol. 31, 427–436, 1983) and van Voorhuizen et al. (Thromb. Haemostas. 52(3), 350–353, 1984).

Total protein concentration was determined by absorption measurements at 280 nm ($A_{280}$). Concentration (mg/ml) for AT-III solutions was calculated using the coefficient of 6.4 IU/mg. Specific activity (SA) of AT-III was defined as the ratio between heparin cofactor activity calculated as IU/ml and $A_{280}$.

EXAMPLES

Example 1

Separation of AT-IIIα and AT-IIIβ by Hydroxyapatite Chromatography

A sample of human antithrombin having a purity of >95%, prepared according to methods known in the art (cf. Miller-Andersson et al. (1974) Thrombosis Research 5, 439–452) was used to analyze the alpha and beta forms of antithrombin.

The antithrombin sample was chromatographed using an HPLC system, equipped with a hydroxyapatite (75×7.5 mm ID, 5 μm, pore size 1000 Å) analytical column that was equilibrated in 10 mM sodium phosphate, 0.01 mM calcium chloride, pH 6.8. The injection volume of antithrombin (6.8 mg/ml) was 25 μl, and the flow rate was 0.5 ml/min at room temperature. Elution was carried out by mean of a segmented gradient; first an isocratic wash period (0 to 5 min) in equilibration buffer, then a short gradient was run (5 to 8 min) to 110 mM sodium phosphate, then a 17 min isocratic run, followed by a linear gradient (25 to 35 min) up to 500 mM sodium phosphate. Detection was carried out by measuring UV absorbance at 280 nm. AT-IIIα and AT-IIIβ eluted at the retention times 16 and 35 minutes, respectively (FIG. 1). Purified AT-IIIα and AT-IIIβ, obtained according to known methods (cf. Peterson, C. B. & Blackburn, M. N. (1985) J. Biol. Chem. 260, 610–615), were used as control samples and gave the same retention times as above when they were analyzed in the same way. No other peaks than AT-IIIα and AT-IIIβ appeared in the chromatogram. The peaks were separated with good resolution and the results showed that the AT-III sample contained about 0.7% of AT-IIIβ, based on the integrated area. Purified histidine-rich glycoprotein gave a longer retention time than AT-IIIβ when analyzed in the same system.

Example 2

Purification of AT-IIIα and AT-IIIβ by Hydroxyapatite Chromatography

An AT-III sample, 450 mg of the same quality as described in Example 1, in 30 ml 10 mM sodium phosphate, pH 6.8, is suitable to be chromatographed using a chromatographic system, equipped with a hydroxyapatite, 15 μm particle size, preparative column (35×2.5 cm ID) equilibrated in 10 mM sodium phosphate, 0.01 mM calcium chloride, pH 6.8. The flow rate of 3 ml/min at a temperature of +4° C. to +8° C. is appropriate for the purification. Elution by means of a segmented gradient: first a 45 min isocratic run in equilibration buffer during sample loading and washing, then a linear gradient (0.5 h) to 110 mM sodium phosphate, followed by an isocratic run (2.6 h), and finally a linear gradient (1.5 h) up to 500 mM sodium phosphate. Detection by measuring UV absorbance at 280 nm. AT-IIIα and AT-IIIβ elute after approximately 2 and 5 h, respectively.

Instead of hydroxyapatite having a particle size of 15 μm, other types of hydroxyapapatite could conveniently be used for purification in a larger scale, e.g. Macro-Prep® ceramic hydroxyapatite (Bio-Rad; particle size 80 μm).

What is claimed is:

1. A process for separating an AT-IIIα isoform from an AT-IIIβ isoform, comprising the steps of:
   (i) providing a solution comprising AT-IIIα and AT-IIIβ;
   (ii) contacting the solution with a calcium hydroxyphosphate-based adsorbent; and
   (iii) eluting an isoform of AT-III.

2. The process according to claim 1 wherein the contacting and eluting are carried out by column chromatography.

3. The process according to claim 1 wherein the eluted isoform is AT-IIIα.

4. The process according to claim 3 wherein AT-IIIα is eluted from the calcium hydroxyphosphate-based adsorbent with a buffer having a phosphate concentration of from about 50 mM to about 150 mM.

5. The process according to claim 1 wherein the eluted isoform is AT-IIIβ.

6. The process according to claim 5 wherein AT-IIIβ is eluted from the calcium hydroxyphosphate-based adsorbent with a buffer having a phosphate concentration of from about 150 mM to about 400 mM.

7. The process according to claim 1 wherein the calcium hydroxyphosphate-based adsorbent is hydroxyapatite.

8. The process according to claim 1 wherein the contacting and eluting are carried out at a pH of from about 6.0 to about 7.5.

9. The process according to claim 1, wherein the solution comprising AT-IIIα and AT-IIIβ is prepared by a process comprising the steps of:
   (i) providing a Cohn Fraction I supernatant from human plasma;
   (ii) contacting the Cohn Fraction I supernatant with an affinity gel capable of binding AT-III; and
   (iii) eluting a protein fraction binding to the affinity gel.

10. The process according to claim 9 wherein the affinity gel comprises heparin as an affinity ligand.

11. The process according to claim 1 wherein the eluted isoform of AT-III is separated from histidine-rich glycoprotein (HRGP).

* * * * *